US00PP10307P

United States Patent [19]

De Wet

[11] Patent Number: Plant 10,307

[45] Date of Patent: Mar. 31, 1998

[54] PEAR ROOTSTOCK BP3

[75] Inventor: Andries Francois De Wet, deceased, late of Stellenbosch, South Africa, by Louisa Augusta Wilhelmina Catharina du Preez (formerly De Wet, born Brummer), executrix

[73] Assignee: Department of Agriculture, South Africa

[21] Appl. No.: 615,800

[22] Filed: Mar. 14, 1996

[51] Int. Cl.[6] ..... A01H 5/00

[52] U.S. Cl. ..... Plt./36

[58] Field of Search ..... Plt./36

[56] References Cited

U.S. PATENT DOCUMENTS

P.P. 5,573 10/1985 Brooks ..... Plt./36

OTHER PUBLICATIONS

Republic of South Africa, Certificate of grant of a Plant Breeder's Right, No. ZA 80061.

*Primary Examiner*—James R. Feyrer

*Attorney, Agent, or Firm*—Chernoff, Vilhauer, McClung & Stenzel

[57] ABSTRACT

A new variety of pear rootstock selected from a family of seedling pear trees germinated from seed collected from a wild pear tree. The subject variety produces hearty pear trees having high yield. The rootstock is compatible with all major commercial pear varieties. The variety roots easily and reproduces readily by hardwood cuttings.

3 Drawing Sheets

BACKGROUND AND SUMMARY OF THE INVENTION

The original plant of this new pear rootstock variety was a member of a family of approximately one hundred (100) seedling pear trees of unknown parentage which germinated from seeds collected in 1928 from a wild pear (*Pyrus communis*) at Elsenburg in the Republic of South Africa.

The subject seedling was selected in 1930 by Dr. A. F. DeWet, a former Research Horticulturist at the Fruit and Fruit Technology Research Institute at Stellenbosch, South Africa.

The BP3 rootstock has been tested and is now being released because of the high production of trees grafted thereon (Tables 1, 2 and 3) and the relative ease with which it roots. In experimental plantings at Stellenbosch with tree spacing of 4.4 m×3.5 m, our new BP3 rootstock consistently outperformed four other pear rootstocks. (Tables 1 and 3.) Trees on BP3 stocks in full bearing are slightly more vigorous than those on seedling stocks and are considered full-sized trees when mature. BP3 rootstocks are considered "non-dwarfing" by industry standards in use today.

BP3 has been virus-tested and is believed to be free of all known virus and virus-like diseases.

The new variety has been reproduced asexually by hardwood cuttings in Stellenbosch, South Africa. All subsequent generations have been true to form in all respects.

The following tables compare production of Packham's Triumph and Bon Chretien pear trees (both are commercial unpatented varieties) grown on the subject rootstock and four other rootstocks.

TABLE 1

The effect of five different rootstocks on trunk cross-sectional area and productions of Packham's Triumph and Bon Chretien.

| Rootstock | Trunk cross-sectional area ($cm^2$) | Cumulative production 12th leaf (kg/tree) | Production efficiency ($kg/cm^2$) |
|---|---|---|---|
| | Packham's Triumph | | |
| BP1 | 116,67 | 350,30 | 3,00 |
| BP2 | 140,31 | 368,10 | 3,62 |
| BP3 | 238,19 | 482,00 | 2,02 |
| Quince A | 64,82 | 141,20 | 2,18 |
| Seedling | 183,96 | 326,50 | 1,77 |
| | Bon Chretien | | |
| BP1 | 129,75 | 326,40 | 2,52 |
| BP2 | 228,03 | 382,40 | 1,68 |
| BP3 | 288,68 | 418,70 | 1,45 |
| Quince A | 774,46 | 146,10 | 1,96 |
| Seedling | 180,53 | 213,60 | 1,18 |

TABLE 2

Cumulative Average Production of Packham's Triumph Pear on five different rootstocks at planting width 4.4 m × 3.5 m. (Kg/Tree)

| Rootstock | 6th year | 7th year | 8th year | 9th year | 10th year | 11th year | 12th year |
|---|---|---|---|---|---|---|---|
| BP1 | 50 | 87 | 132 | 196 | 248 | 275 | 350 |
| BP2 | 47 | 73 | 124 | 187 | 246 | 288 | 368 |
| BP3 | 48 | 90 | 170 | 246 | 302 | 360 | 482 |
| Quince A | 12 | 23 | 48 | 71 | 89 | 120 | 141 |
| Seedling | 35 | 70 | 124 | 185 | 240 | 286 | 326 |

TABLE 3

Cumulative Average Production of Bon Chretien Pear on five different rootstocks at actual planting width 4.4 m × 1.5 m. (Kg/Tree)

| Rootstock | 6th year | 7th year | 8th year | 9th year | 10th year | 11th year | 12th year |
|---|---|---|---|---|---|---|---|
| BP1 | 35 | 61 | 82 | 123 | 164 | 198 | 326 |
| BP2 | 38 | 59 | 78 | 149 | 261 | 303 | 382 |
| BP3 | 44 | 64 | 94 | 123 | 275 | 329 | 418 |
| Quince A | 10 | 15 | 26 | 52 | 92 | 123 | 146 |
| Seedling | 25 | 36 | 48 | 75 | 132 | 175 | 213 |

When compared to the O.H.X.F. variety #282, a patented clonal pear rootstock variety which produces trees similar in size to our BP3 variety, the following differences are noted:

| Character | BP3 | O.H.X.F. 282 |
|---|---|---|
| 1. Yield efficiency | Excellent (see Tables 1, 2 and 3) | Average (similar to seedling) |
| 2. Resistance to fire Blight (*Erwinia amylovora*) | Average | Highly resistant |
| 3. Strength of one year growth | Stiff | Flexible |
| 4. Branching of current season growth | Many | Almost branchless |
| 5. Leaf shape | Narrow - Lenceolate | Broad - Ovate |
| 6. Fruit skin color | Green-yellow with no over-color | Yellow with reddish russet-like over-color |
| 7. Fruit shape | Wider than long | Longer than wide |

DETAILED DESCRIPTION

The following is a detailed description of BP3 growth characteristics as observed on one-year-old shoots produced from hardwood cutting and on nine (9) year old stock plants growing at the research station site near Stellenbosch, South Africa. The characteristics described are those most often seen and used in the identification of a clonally propagated rootstock.

General color terms are used in accordance with their ordinary dictionary significance.

Description of Vegetative Characteristics

Terminology in accordance with S. B Jones & A. E. Luchsinger: *Plant Systematics,* Sec. Ed 1987 McGraw-Hill.

Color: Color characteristics of the foliage, fruit, bark and fall color of the subject variety do not differ noticeably and are not unique when compared with other fruiting and rootstock varieties of Pyrus communis except as noted.

Figure 1:
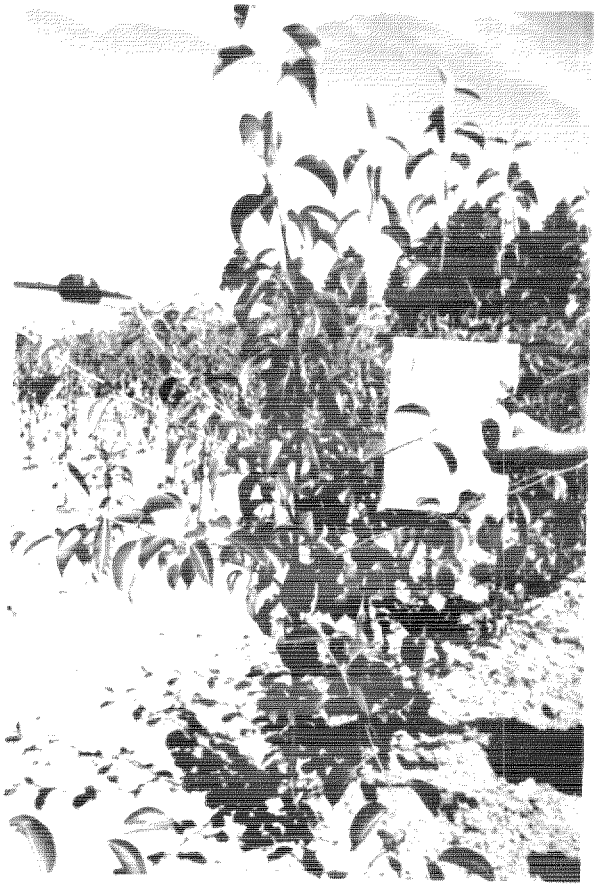
FIG. 1 shows a young tree of the subject variety.

General habit: (FIG. 1).
- *Strength of growth.*—Vigorous, stiff.
- *Habit.*—Upright.
- *Branching.*—Many, stiff.

Vegetative shoots:
- *Bark color.*—Light brown.
- *Pubescence.*—Glabrous.
- *Lenticels.*—Many.
- *Growth.*—Slight zig-zag effect.

Figure 2:
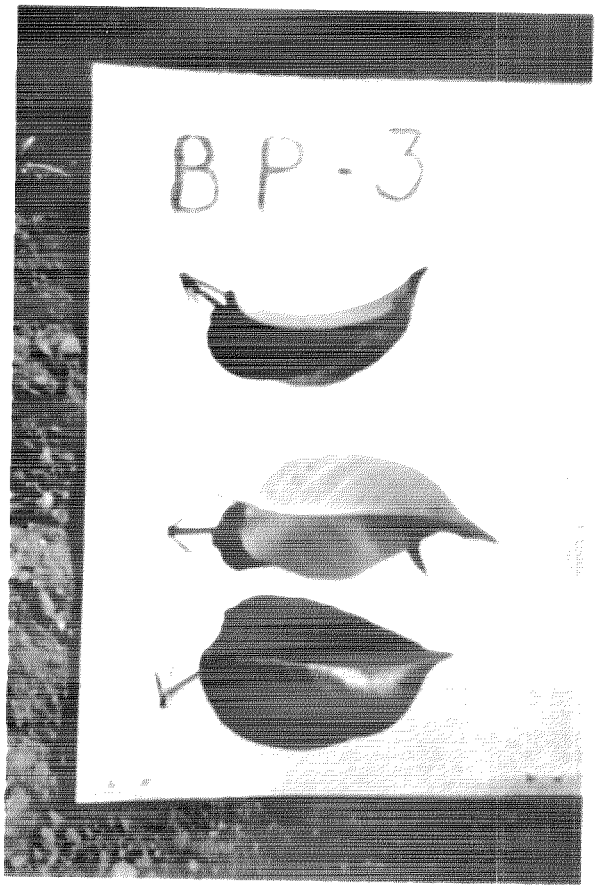
FIG. 2 shows leaves from a tree of the subject variety.

Leaves: (FIG. 2).
- *Size.*—Average 77.3 mm×53.6 mm.
- *Shape.*—Lanceolate.
- *Base.*—Rounded.
- *Apex.*—Accuminate.
- *Serrations.*—Serrate, shallow.
- *Internode length.*—Average —25 mm.
- *Arrangement.*—Alternate.
- *Color.*—Top surface—green; bottom surface—pale green.
- *Anthocyanin.*—Slight.

Leaf scars:
- *Shape.*—Very broad V-shaped/semilunate.
- *Color.*—Dark brown.

Petioles:
- *Shape.*—Elliptic.
- *Length.*—Medium, 1–2 cm.
- *Color.*—Light Green.
- *Pose.*—Medium angle of 30–60 degrees.

Stipules:
- *Size.*—Medium 10 mm, conspicuous, subulate.
- *Color.*—Light green.
- *Pose.*—Reposed along petiole.
- *Margin.*—Entire.

Lateral buds:
- *Size.*—Large.
- *Shape.*—Angular, slightly held out.
- *Color.*—Dark brown.
- *Pubescence.*—Pubescent.

Apical buds:
- *Size.*—Larger than lateral buds.
- *Shape.*—Acute with scales.
- *Color.*—Dark brown.
- *Pubescence.*—Pubescent.

Dormant Plant

Shoots:
- *Size.*—Diameter at base 1–1.5 cm, stiff.
- *Bark color.*—Light brown.
- *Pubescence.*—None.
- *Nodes.*—Same diameter as internodes with inconspicuous shoulder at the leaf scar.
- *Internodes.*—Regularly spaced, fairly smooth but with conspicuous lenticels.
- *Distance between nodes.*—Average—25 mm.

Figure 3:
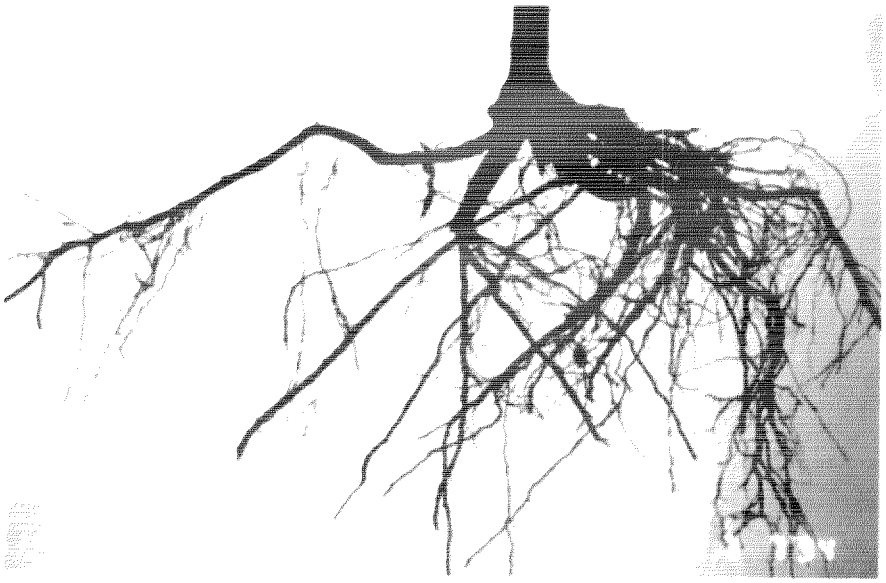
FIG. 3 shows the roots of a tree of the subject variety.

Rooting characteristics: Relative easy to root when compared to other clonally propagated pear (*Pyrus*) rootstocks; roots develop where callus tissue is formed at the tip along the edge of the cut (FIG. 3).

Flower and Fruit Characteristics

Flowers:
- *Inflorescence.*—Mean number of flowers, 7.9 per lateral flower bud.
- *Flower type.*—Single.
- *Flower color.*—White.
- *Petal length.*—Mean 15 mm.
- *Shape of base of petal.*—Flat.
- *Sepal length.*—Medium.
- *Sepal position.*—Pressed against the corolla.

*Stigma position as compared with the anthers.*—Above.
*Anther size.*—Medium.
*Anther count.*—Average—16.
*Anther color.*—Pale yellow.
*Pedicel pubescence.*—Sparse.
*Pollen.*—Functional.

Fruit: External evaluation when ripe (No commercial value):
*Time of fruit ripening:.*—Late February in Stellenbosch, So. Africa.
*Symmetry (in longitudinal section).*—Symmetric.
*Shape (in profile view).*—Convex.
*Position of maximum diameter.*—Towards middle.
*Ground color of skin.*—Green-yellow.
*Over-color of skin.*—Absent.
*Tendency to color by the sun.*—Absent/very little.
*Amount of russet.*—Mediums.
*Position of russet.*—Distributed over the whole fruit.
*Number of lenticels.*—Many.
*Conspicuousness of lenticels.*—Conspicuous.
*Length of stalk.*—Medium.
*Thickness of stalk.*—Thin.
*Shape of stalk.*—Straight.
*Insertion of stalk.*—At right angles to axis.
*Cavity of stalk.*—Medium.
*Size of eye.*—Medium.
*Opening of eye.*—Open.
*Pose of sepals.*—Spreading.
*Length of sepals.*—Medium.
*Width of eye basin.*—Medium.
*Margin of eye basin.*—Slightly ribbed.
*Length.*—43.1 mm average.
*Diameter.*—50.9 mm.
*Size (length × diameter).*—2195.1.
*Mass (weight).*—65.8 g/fruit.

Fruit: Internal evaluation when ripe:
*Diameter of core.*—2.3 mm.
*Type of core.*—Hardened.
*Shape of cells of core.*—Rounded.
*Shape of seeds.*—Ovate.
*Color of seed (dried).*—Dark brown.
*Texture of flesh.*—Fine.
*Juiciness of flesh.*—Weak.
*Taste of flesh.*—Intermediate.

General Characteristics

Root suckering: Very limited.
Dwarfing: None.
Precocity: Trees grafted on clone rootstocks bear earlier than on seeding rootstock.
Adaptability to soil type: Does well on sandy loam to clay loam soils.
Compatibility: Graft compatible with all major commercial pear cultivars.
Size control potential: None.
Root anchorage: (FIG. 3) Good, but with a more shallow root system than a tree grown on seedling rootstock (FIG. 3).
Hardiness: Hardy in most pear growing areas in the Republic of South Africa.
Disease status: Tested and found free of all known virus and virus-like diseases of pear.

General Guideline for Propagation

BP3 is a vigorous rootstock and a safe choice for pear trees planted on the poorer soils. A 5 m×3 m planting width is recommended as a general guide. Preference should also be given to this rootstock for high density planting.

As with most clonal pear rootstocks, BP3 does not root easily from stool beds. Cuttings are the only practical method of vegetative propagation.

The BP3 pear rootstock is propagated most easily and successfully by use of hardwood cutting.

The successful propagation of plants of BP3 by hardwood cuttings depends on internal anatomical and physiological factors as well as the influence of external factors. Since cuttings are only a continuation of the mother stockplant shoot, it is very important that good cultural practices like soil preparation, irrigation, weed, disease and pest control, etc., take place in the motherstock block.

BP3 produces secondary shoots which do not root as well as the primary shoots and they should not be used for propagation purposes.

BP3 cuttings should be cut off apically and basally near a bud (>2 mm). This prevents cut die-back. Die-back on BP3 hardwood cuttings occurs more frequently on cuttings propagated in sandy soil types.

Basal wounding of BP3 hardwood cuttings promotes rooting. A hormone treatment should be applied immediately following wounding to ensure effective uptake.

BP3 cuttings will root best in warm, well drained, sandy-loam to loamy soils with a low water holding capacity.

Overhead cooling and wind protection is often beneficial in the rooting process.

It is claimed:

1. A new variety of pear tree, referred to by the cultivar designation BP3, substantially as herein shown and described, characterized particularly by its ability to serve as a rootstock for grafting of pear tree cultivars to produce pear trees which have a very high yield efficiency, are hardy and are compatible with all major commercial pear varieties, and by its early bearing habit when compared to the commercially used seedling rootstocks and its ability to reproduce readily by vegetative means particularly by hardwood cuttings.

* * * * *

UNITED STATES PATENT AND TRADEMARK OFFICE

CERTIFICATE OF CORRECTION

PATENT NO. : PP10307

DATED : 03/31/98

INVENTOR(S) : Andries Francois De Wet

It is certified that error appears in the above-identified patent and that said Letters Patent is hereby corrected as shown below:

Column 5, line 17, Under heading "Fruit,"
"Amount of russet"
Delete: [Mediums] Insert: Medium Signed and Sealed this
Fourth Day of January, 2000

*Attest:*

*Attesting Officer*

*Acting Commissioner of Patents and Trademarks*